United States Patent
Byrd et al.

(10) Patent No.: US 10,194,885 B2
(45) Date of Patent: Feb. 5, 2019

(54) AUTOMATIC MONITORING FOR AND DETECTION OF TISSUE POP

(71) Applicant: St. Jude Medical, Atrial Fibrillation Division, Inc., St. Paul, MN (US)

(72) Inventors: Israel A. Byrd, Richfield, MN (US); Jeffrey M. Fish, Maple Grove, MN (US); Lynn E. Clark, Maplewood, MN (US); Saurav Paul, Minneapolis, MN (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 121 days.

(21) Appl. No.: 14/369,069

(22) PCT Filed: Oct. 2, 2012

(86) PCT No.: PCT/US2012/058427
§ 371 (c)(1),
(2) Date: Jun. 26, 2014

(87) PCT Pub. No.: WO2013/101321
PCT Pub. Date: Jul. 4, 2013

(65) Prior Publication Data
US 2014/0358038 A1 Dec. 4, 2014

Related U.S. Application Data

(60) Provisional application No. 61/582,004, filed on Dec. 30, 2011.

(51) Int. Cl.
*A61B 7/04* (2006.01)
*A61B 7/00* (2006.01)
(Continued)

(52) U.S. Cl.
CPC .............. *A61B 7/04* (2013.01); *A61B 5/4848* (2013.01); *A61B 5/725* (2013.01); *A61B 5/742* (2013.01);
(Continued)

(58) Field of Classification Search
CPC ......... A61B 7/04; A61B 7/4848; A61B 5/742; A61B 5/7405; A61B 5/4836; A61B 5/725
See application file for complete search history.

(56) References Cited

U.S. PATENT DOCUMENTS

| 5,733,281 A | 3/1998 | Nardella |
| 6,233,476 B1 | 5/2001 | Strommer et al. |

(Continued)

FOREIGN PATENT DOCUMENTS

| CN | 103209654 A | 7/2013 |
| JP | 2005-199072 A | 7/2005 |
| WO | 2011/062681 A1 | 5/2011 |

OTHER PUBLICATIONS

Kotini, P. et al. "Detection of Microbubble Formation During Radiofrequency Ablation Using Phonocardiography," Europace, Feb. 2006, vol. 8, No. 5, pp. 333-335, ISSN 1099-5129.

*Primary Examiner* — Daniel L Cerioni
*Assistant Examiner* — Yasmeen S Warsi
(74) *Attorney, Agent, or Firm* — Dykema Gossett PLLC

(57) ABSTRACT

A system that automatically detects a myocardial barotrauma (i.e., tissue pop) event so that proper post-procedure care can be given includes an electronic control unit (ECU), a computer-readable memory coupled with the ECU, and detection logic stored in the memory configured to be executed by the ECU. The detection logic is configured to receive a signal generated by an electro-acoustic transducer related to acoustic activity within the patient, monitor the signal for a pre-determined indication of a barotrauma event, and output a notification when the pre-determined (Continued)

indication is detected. The transducer can be integrated with an extra-body patch that includes one or more electrodes for use with a medical device navigation system.

14 Claims, 7 Drawing Sheets

(51) Int. Cl.
*A61B 5/00* (2006.01)
*A61B 18/14* (2006.01)
*A61B 5/053* (2006.01)
*A61B 18/00* (2006.01)
*H04R 17/02* (2006.01)

(52) U.S. Cl.
CPC .............. *A61B 5/7405* (2013.01); *A61B 7/00* (2013.01); *A61B 18/1492* (2013.01); *A61B 5/0538* (2013.01); *A61B 5/4836* (2013.01); *A61B 2018/0069* (2013.01); *A61B 2018/0088* (2013.01); *A61B 2018/00351* (2013.01); *A61B 2018/00577* (2013.01); *A61B 2018/00642* (2013.01); *A61B 2018/00898* (2013.01); *H04R 17/02* (2013.01)

(56) References Cited

U.S. PATENT DOCUMENTS

| | | |
|---|---|---|
| 6,498,944 B1 | 12/2002 | Ben-Haim et al. |
| 6,690,963 B2 | 2/2004 | Ben-Haim et al. |
| 6,788,967 B2 | 9/2004 | Ben-Haim et al. |
| 7,197,354 B2 | 3/2007 | Sobe |
| 7,263,397 B2 | 8/2007 | Hauck et al. |
| 7,386,339 B2 | 6/2008 | Strommer et al. |
| 7,536,218 B2 | 5/2009 | Govari et al. |
| 7,996,055 B2 | 8/2011 | Hauck et al. |
| 8,449,535 B2 | 5/2013 | Deno et al. |
| 8,517,031 B2 | 8/2013 | MacGregor et al. |
| 2003/0204184 A1 | 10/2003 | Ferek-Patric |
| 2005/0080334 A1* | 4/2005 | Willis .............. G01S 5/22 600/424 |
| 2007/0060833 A1 | 3/2007 | Hauck |
| 2008/0013747 A1* | 1/2008 | Tran .............. A61B 5/0452 381/67 |
| 2008/0177258 A1 | 7/2008 | Govari et al. |
| 2010/0168568 A1* | 7/2010 | Sliwa .............. A61B 8/12 600/439 |
| 2010/0168572 A1 | 7/2010 | Sliwa et al. |
| 2011/0118727 A1 | 5/2011 | Fish et al. |
| 2012/0158011 A1 | 6/2012 | Sandhu et al. |
| 2013/0066193 A1 | 3/2013 | Olson et al. |

\* cited by examiner

AUTOMATIC MONITORING FOR AND DETECTION OF TISSUE POP

CROSS-REFERENCE TO RELATED APPLICATION

This application is a national stage entry of PCT/US2012/058427, filed Oct. 2, 2012, which claims the benefit of U.S. provisional application No. 61/582,004, filed Dec. 30, 2011, both of which applications are hereby incorporated by reference in their entirety as though fully set forth herein.

BACKGROUND OF THE INVENTION a. Field of the Invention

This disclosure relates to systems and methods for automatic detection of barotrauma in the tissue of a patient. More specifically, the instant disclosure relates to systems and methods for automatic detection of a myocardial barotrauma event during an ablation procedure.

b. Background Art

During ablation procedures, such as, for example, cardiac ablation procedures, adverse events can occur that result in damage to the tissue being ablated, such as charring of the tissue, localized coagulation, tamponade, and effusion. In radio frequency (RF) ablation, one such adverse event, though rare, is the occurrence of myocardial barotrauma, also known as "steam pop" and/or "tissue pop". Tissue pop may occur, for example, when fluid in the tissue boils as a result of the RF energy applied to the tissue.

Because tissue pop may cause significant tissue damage, proper post-procedure care requires that a physician know if a tissue pop event occurred during an ablation procedure. But symptoms of tissue pop often are not manifest until several hours after a procedure, during which time a patient may not have received additional monitoring and may have taken blood thinning or other medication that can exacerbate tissue pop symptoms. As a result, undiagnosed tissue pop can lead to sub-optimal post-operative patient care.

Known non-invasive methods of detecting tissue pop are dependent on the senses of the electrophysiologist or physician performing the ablation procedure. For example, the electrophysiologist may hear the noise made by the tissue pop, or may feel the pop as a vibration on the catheter. But such detection methods are unreliable. The surgical environment may be too noisy to hear a tissue pop event, and the electrophysiologist or physician may not feel a tissue pop because the catheter tip has been moved off of the popping tissue or may mistake a tissue pop transmitted up the catheter for normal catheter movement.

There is therefore a need for systems and methods for detecting a tissue pop event that minimizes or eliminates one or more of the problems set forth above.

BRIEF SUMMARY OF THE INVENTION

It is desirable to provide a reliable, non-invasive system that automatically detects a myocardial barotrauma (i.e., tissue pop) event, for example only, and automatically generates a notification of that event so that proper post-procedure treatment can be given. Such a system includes an electronic control unit (ECU), a computer-readable memory coupled with the ECU, and detection logic stored in the memory configured to be executed by the ECU. The detection logic is configured to receive an electrical signal indicative of acoustic activity within a body, monitor the signal for a pre-determined indication of a barotrauma event, and generate a notification output when the pre-determined indication is detected. In an embodiment, the system further includes storage memory coupled with the ECU, and the detection logic is further configured to store data in the storage memory related to a barotrauma event when the pre-determined indication is detected. The data may include a portion of the signal beginning at a first time before the barotrauma event and ending at a second time after the barotrauma event.

The system may perform a variety of signal processing functions on the electrical signal. In an embodiment, the detection logic may be configured to filter and/or apply an amplification algorithm to the signal to amplify an occurrence of the pre-determined indication of a barotrauma event for improved event detection.

In a further embodiment, the system includes an electro-acoustic transducer configured to be disposed within the body or coupled with the exterior of the body of the patient. The transducer generates an electrical signal indicative of acoustic activity within the patient that is monitored by the ECU. The transducer can be incorporated with a patch configured to be coupled to the body of the patient, and the patch can include a body surface electrode for use with a medical device positioning and navigation system.

A computer-implemented method for detecting tissue pop during an ablation procedure on a patient includes a number of steps. A first step includes receiving an electrical signal indicative of acoustic activity within the patient. A second step includes monitoring the signal for a pre-determined indication of a myocardial barotrauma event. A third step includes generating a notification output when said pre-determined indication is detected. A further step includes storing data related to the barotrauma event.

The foregoing and other aspects, features, details, utilities, and advantages of the present disclosure will be apparent from reading the following description and claims, and from reviewing the accompanying drawings.

DETAILED DESCRIPTION OF THE INVENTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
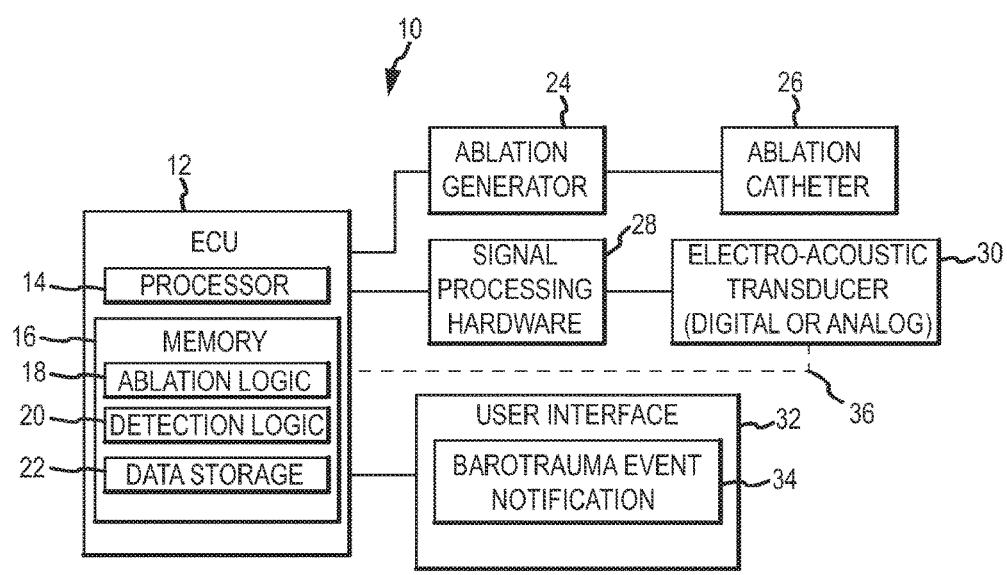
FIG. 1 is a schematic and block diagram view of a system for automatically detecting a myocardial barotrauma event during an ablation procedure.

Referring now to the drawings wherein like reference numerals are used to identify identical or similar components in the various views, FIG. 1 is a schematic view of an embodiment of a system 10 for automatically detecting a myocardial barotrauma (i.e., tissue pop) event during an ablation procedure. The system 10 includes an electronic control unit (ECU) 12 with an electronic processor 14 and a computer-readable memory 16 which itself includes ablation logic 18, detection logic 20, and data storage memory 22. The system 10 further includes an ablation generator 24, an ablation catheter 26, signal processing hardware 28, an electro-acoustic transducer 30, a user interface 32, and a barotrauma event notification 34.

The ablation catheter 26 is provided for treatment of a tissue in a patient such as, for example, cardiac tissue. The catheter 26 ablates tissue through the controlled application of RF energy or power through one or more electrodes. The ablation catheter 26 can be a conventional ablation device known in the art.

The ablation generator 24 generates, controls, and delivers RF energy for the ablation catheter 26. The generator 24 includes an RF ablation signal source configured to generate an ablation signal that is output across a pair of source connectors: a positive polarity connector which can connect to an electrode on the catheter 26; and a negative polarity connector which may be electrically connected by conductors or lead wires to patch electrodes on the patient's body (not shown). The generator 24 is configured to generate an ablation signal at a predetermined frequency in accordance with one or more user specified parameters (e.g., power, time, etc.) and under the control of various feedback sensing and control circuitry as known in the art. For example, the ablation signal can have a frequency within a range of about 1 kHz to over 500 kHz or, more specifically, between about 450 kHz and about 500 kHz. In an embodiment, the ablation signal has a frequency of about 485 kHz. RF ablation embodiments may and typically will include other structure(s) not shown in FIG. 1, such as one or more body surface electrodes (skin patches) for application onto the body of a patient (e.g., an RF dispersive indifferent electrode/patch, shown diagrammatically in FIG. 5), and an irrigation fluid source (gravity feed or pump). RF ablation generator 24 may comprise a commercially available unit sold under the model number IBI-1500T RF Cardiac Ablation Generator, available from St. Jude Medical, Inc.

The electro-acoustic transducer 30 is provided to translate acoustic activity inside the patient's body into an electrical signal (either digital or analog) that can be monitored for an indication of tissue pop. In various embodiments, the transducer 30 can be configured to be coupled to the exterior of the patient's body, advantageously allowing for non-invasive tissue pop detection. The transducer 30 can be part of any apparatus fit for this purpose such as, for example, a digital stethoscope or analog stethoscope. If digital, the transducer 30 should have a sufficiently high sampling rate to detect tissue pop such as, for example only, about one thousand hertz or more. In an embodiment, the transducer 30 may be a part of a digital stethoscope manufactured by Thinklabs Medical LLC of Centennial, Colo. The electro-acoustic transducer 30 can be incorporated into another apparatus or structure that is coupled to the patient's body. For example, the transducer 30 can be a part of a patch for use with a medical device positioning and navigation system. An exemplary embodiment of such a patch is shown in FIG. 6. In another embodiment, the transducer 30 can be incorporated into an ablation dispersive patch, as shown diagrammatically in FIG. 5. In yet another embodiment, the transducer 30 can be a mechanically-independent apparatus that is placed on the patient's body such as, for example only, a dedicated patch. In still another embodiment, the transducer 30 may be configured to be coupled with an elongate medical device disposed within the body of a patient. Such an embodiment is further described with respect to FIG. 3.

Referring to FIG. 1, the electro-acoustic transducer 30 should be constructed, modified, and/or implemented such that it is viable for use in an operating room environment. For example, it should be capable of withstanding a defibrillation shock to the patient without becoming disabled and without transmitting the voltage from the shock to the ECU 12 or other electrical equipment.

The signal processing hardware 28 may be electrically coupled with the transducer 30 and with the ECU 12 and may be configured to perform one or more of a variety of signal processing functions on the signal generated by the transducer 30. The hardware 28 can receive a first signal generated by the transducer 30, perform at least one processing function on the first signal to create a second signal, and provide the second signal to the ECU 12. Processing functions can include, e.g., low-pass filtering, band-pass filtering, attenuation, and/or amplification. For example, the hardware 28 can low-pass filter the signal to eliminate frequencies of the ablation generator 24 and other components in the operating environment, such as excitation signals from a medical device mapping, positioning, and navigation system. The hardware can also high-pass filter the signal to eliminate frequencies of normal biological activity. An exemplary embodiment of the hardware 28 can include a tuned inductor-capacitor trap.

The user interface 32 is provided to allow a user, such as an electrophysiologist or physician, to interact with the system 10. To this end, the user interface 32 can receive user input and give output to the user through a variety of apparatus including, for example only, a mouse, a keyboard, a display, a joystick, a foot pedal, and/or other apparatus known in the art. The barotrauma event notification 34 is incorporated into the interface 32 and is provided to alert a physician, electrophysiologist, or other individual that a tissue pop event has occurred. The notification 34 can be implemented with any mechanism or device capable of alerting the electrophysiologist or physician that tissue pop has occurred such as, for example, a visual, audible, or tactile mechanism or device, or a combination thereof. For example only, the notification can be implemented with an LED or other light, a binary indicator on a computer display or other display (i.e., a "virtual LED" with at least two operating states: ON and OFF), a continuous display on a computer display or other display, and/or an audible alarm. The content of a visual embodiment of notification 34 can be discrete or continuous in nature and can include, but is not limited to, an alert light, an alert message, an alert sound, and a continuous waveform. In an embodiment, when a tissue pop event is detected, the notification 34 can comprise a pop-up window in a computer display that shows a waveform of the signal from the transducer 30 when a tissue pop event is detected.

The ECU 12 is responsive to the electrical signal from the transducer 30 (directly or through the signal processing hardware 28) to provide commands to the user interface 32 and/or the ablation generator 24. To this end, the ECU 12 is operatively coupled with the ablation generator 24, the signal processing hardware 28, and the user interface 32. In another embodiment, the ECU 12 may be connected directly to the transducer 30 (i.e., the system may contain no hardware for signal processing), as illustrated by dashed line 36. The ECU 12 may receive a continuous signal, determine if a pre-determined indication of a tissue pop event is present on the signal, and generate a notification output—i.e., activate and/or control notification 34—when a tissue pop event is detected. The ECU 12 can also exercise a degree of control over the ablation generator 24 based on the contents of the electrical signal. Further, the ECU 12 can store data related to a tissue pop event and/or other information related to the procedure.

To control the ablation generator 24, the ECU 12 executes ablation logic 18, which is provided on computer-readable memory 16 and is configured both to drive and to receive feedback from the ablation generator 24. Based on the state of the system 10, the ablation logic 18 can decide whether the ablation generator 24 should be enabled to provide RF energy to the ablation catheter 26 or should be disabled to cut off the supply of RF energy. The ECU 12 can then enable or disable the ablation generator. For example, in an embodiment, if tissue pop (i.e., a pre-determined indication of tissue pop) is detected, the ablation logic 18 determines that the ablation generator 24 should be disabled, and the ECU 12 disables the generator 24.

In an embodiment, the ECU 12 can be connected to the ablation generator 24 for feedback purposes only—i.e., ablation logic 18 is not provided or the ECU 12 does not execute ablation logic 18 to control the ablation generator 24. In such an embodiment, control of the ablation generator can be performed entirely by the physician or electrophysiologist, though the ECU 12 can still receive feedback through the ablation generator 24 for, e.g., monitoring impedance at an ablation site.

To determine if a tissue pop event has occurred and activate/control notification 34, the ECU 12 executes detection logic 20, which is provided on computer readable memory 16. The detection logic 20 is configured to receive an electrical signal indicative of acoustic activity within a patient's body, monitor the signal for a pre-determined indication of tissue pop, and generate a notification output when the pre-determined indication is detected. The predetermined indication can be a particular pattern in the received signal such as, for example only, a signal spike having a relatively short temporal duration (e.g., about 3 milliseconds or less; more specifically, about 2-3 milliseconds). The detection logic 20 can also be configured to perform one or more of a variety of signal processing functions on the received signal. Processing functions can include, e.g., low-pass filtering, high-pass filtering, band-pass filtering, attenuation, and/or amplification. For example, the detection logic 20 can apply an amplification algorithm to the signal to amplify an occurrence of a pre-determined indication to make tissue pop easier to distinguish from other biological activity. Signal processing by the detection logic 20 can be in addition to or alternative to processing performed by the signal processing hardware 28. The detection logic 20 can be further configured to store data in data storage memory 22 related to a detected tissue pop event.

In a simplified alternate embodiment of the system 10 (not shown), the transducer 30 can be configured to interface (directly or through signal processing hardware 28) with an ECU 12 with limited processing capability such as, for example, an ECG monitor. In such an embodiment, the transducer 30 can provide a signal indicative of acoustic activity within a patient to the ECG, and the ECG can be configured to display the electro-acoustic signal along with or instead of a traditional ECG waveform. An electrophysiologist or physician could detect a tissue pop event through observation of the displayed signal. Additionally, the ECG could be provided with additional programming (such as detection logic 20) to automatically detect a pre-determined indication of a tissue pop event in the signal and generate a notification output.

In an embodiment (not shown), the system 10 can include apparatus necessary for robotic control of the catheter 26 or another medical device. The robotic system can include a robotic manipulator assembly under the control of the ECU 12 and other components substantially as described in co-pending U.S. patent application Ser. No. 12/970,500, which is hereby incorporated by reference in its entirety as though fully set forth herein. In such a robotic embodiment, the notification output can include a robotic command—i.e., the ECU 12 can be configured to command the robotic manipulator assembly responsive to a detected tissue pop event. For example only, when a tissue pop event is detected, the ECU 12 may issue a command to retract the robotically-controlled ablation catheter away from the tissue being ablated. Such a robotic command can be in addition to as an alternative to other notification output.

Although the system 10 and the other systems described herein are described with reference to RF ablation, it should be understood that automatic detection of tissue pop may find use with other types of ablation energy that heat the tissue such as, for example, ultrasound. Accordingly, neither the system 10 nor its components (e.g., ablation generator 24) are limited to ablation that uses RF ablation energy.

Figure 2:
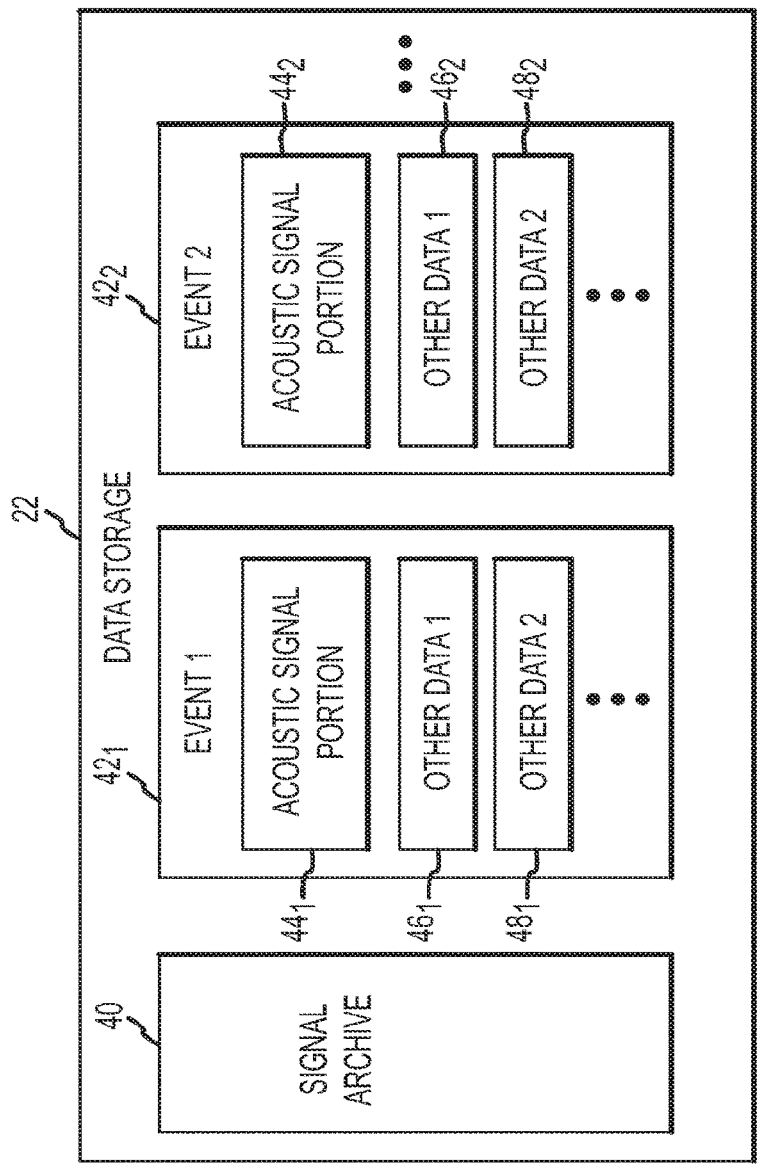
FIG. 2 is a schematic and block diagram view of data storage memory such as may be used in the system of FIG. 1.

FIG. 2 is a diagrammatic view of an exemplary embodiment of data storage memory 22 in which the ECU 12 can store information (e.g., by executing detection logic 20) related to tissue pop events and other data. Storage memory 22 includes a signal archive 40 and a number of event registers for storing data related to tissue pop or other events, with two such registers $42_1$, $42_2$ shown. Each event storage register can include a stored portion 44 of the electrical signal generated by the electro-acoustic transducer 30 and a number of other elements of stored data, with two such elements 46, 48 shown.

During an ablation procedure, the ECU 12 can store the signal received from the transducer 30 in the signal archive 40. The entire signal—i.e., the entire temporal duration of the signal, from the beginning of a procedure to the end of the procedure—can be stored in the signal archive 40, or only a portion of the signal can be stored. Alternatively, the ECU 12 can store a rolling window of the signal in the signal archive 40. For example, the ECU 12 can store the most recent ten seconds of the signal throughout a procedure.

When a tissue pop event is detected, the ECU 12 can store data related to the event in an event register 42. Stored data can include a portion of the electrical signal from electro-acoustic transducer 30 in space 44. For example, a portion of the signal that starts a pre-determined amount of time before the event and ends a pre-determined amount of time after the event can be saved. In an embodiment, the signal portion stored in space 44 for an event can have a duration of about 20 seconds—about 10 seconds before the event through about 10 seconds after the event. Stored data can also include (i.e., data stored in spaces 46, 48, and additional spaces) other information about the procedure, patient, or conditions surrounding a detected tissue pop event. For example, other stored data can include, without limitation, position and orientation (P&O) data showing the location of the ablation catheter 26 when a tissue pop event occurred, other patient data (e.g., ECG), ablation generator settings (e.g., power (W), duration (s), impedance (ohm)), and a timestamp. The stored data can be reviewed by a physician after the procedure to design an effective treatment plan for the patient. The stored data can also be used by the physician or electrophysiologist performing the ablation procedure to better understand the conditions resulting in tissue pop to avoid future tissue pop events.

Although the data storage memory 22 is shown with two event registers $42_1$, $42_2$, any number of event registers can be provided in memory 16. And although each event register is shown with three data elements 44, 46, 48, each register can have any number of data elements. Furthermore, although the ablation logic 18, detection logic 20, and storage memory 22 are shown in FIG. 1 as elements in the same computer-readable memory 16, this is for ease of illustration only. The ablation logic 18, detection logic 20, and data storage memory 22 can be provided in any combination on any number of memory apparatus.

Figure 3:
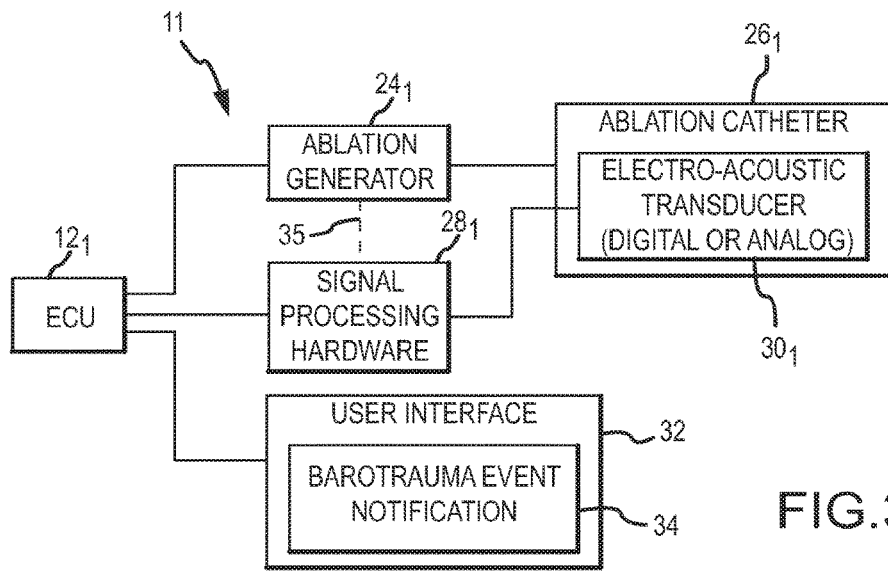
FIG. 3 is a schematic and block diagram view of another system for automatically detecting a myocardial barotrauma event during an ablation procedure.

FIG. 3 is a schematic and block diagram view of an embodiment of a system 11 for automatically detecting a tissue pop event during an ablation procedure. The system 11 includes an ECU $12_1$, an ablation generator $24_1$, an ablation catheter $26_1$, signal processing hardware $28_1$, an electro-acoustic transducer $30_1$, the user interface 32, and the barotrauma event notification output 34. The components of the system 11 have substantially the same elements and functionality as components with the same or similar numerals described above with respect to FIGS. 1-2, except as distinguished below.

The electro-acoustic transducer $30_1$ is intended to be disposed within the body of a patient, and thus is coupled with and/or within the ablation catheter $26_1$. The transducer $30_1$ may be coupled to any portion of the ablation catheter $26_1$, such as a distal portion, a distal tip, or a proximal portion. In an embodiment, the electro-acoustic transducer $30_1$ may be coupled to another medical device, such as a sheath, a diagnostic catheter, and the like.

The ablation generator $24_1$ may be configured to receive a signal indicative of acoustic activity from the transducer $30_1$ (e.g., by way of a common interface for ablation energy, ablation-related signals, and one or more acoustic activity signals) or from the signal processing hardware $28_1$ (as illustrated by phantom line 35). The ablation generator $24_1$ may be configured to act as a pass-through for such acoustic activity signals (i.e., for the signals to continue to the ECU $12_1$), such that the ECU $12_1$ is not independently connected to the transducer $30_1$ or the signal processing hardware $28_1$.

The signal processing hardware $28_1$ and the ECU $12_1$ may each be configured to process a signal indicative of acoustic activity obtained from within the patient's body. For example, the signal processing hardware $28_1$ may be configured to filter, amplify, and/or attenuate a signal based on acoustic activity detected from closer to the source of the activity (i.e., from within the body, rather than from outside the body). The ECU $12_1$ may be similarly configured to filter and/or monitor a signal (e.g., with an embodiment of detection logic 20) based on acoustic activity detected from closer to the source of the activity.

Figure 4:
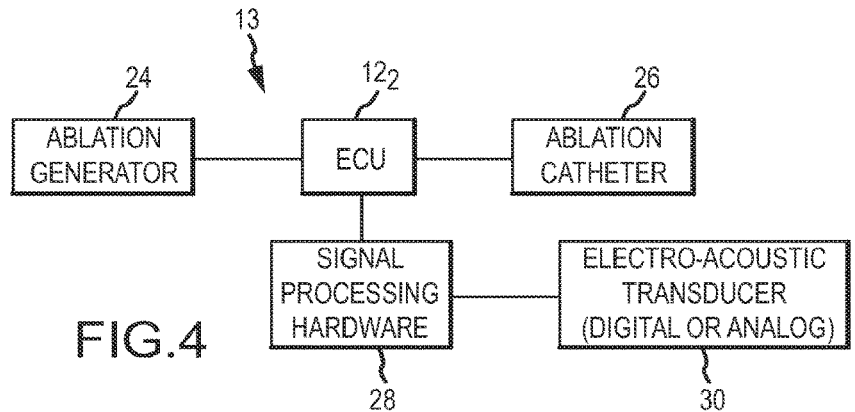
FIG. 4 is a schematic and block diagram view of another system for automatically detecting a myocardial barotrauma event during an ablation procedure.

FIG. 4 is a schematic and block diagram view of a system 13 for automatically detecting a tissue pop event during an ablation procedure. The system 13 includes the ablation generator 24, an ECU $12_2$, the ablation catheter 26, the signal processing hardware 28, and the electro-acoustic transducer 30. The components of the system 13 have substantially the same elements and functionality as components with the same or similar numerals described above with respect to FIGS. 1-2, except as distinguished below.

The system 13 differs from the system 10 in that ablation catheter 26 is coupled to the ECU $12_2$, not directly to the ablation generator 24. In this embodiment, the ECU $12_2$ may act as a pass-through for ablation energy, sensor signals, and other signals between the ablation generator 24 and the ablation catheter 26 during normal operation, while monitoring a signal from the transducer 30 for an indication of tissue pop. When the ECU $12_2$ detects a tissue pop event, the ECU $12_2$ may prevent ablation energy from the ablation generator from reaching the ablation catheter 26 by, for example only, transferring the ablation energy to a "dummy" load in the ECU $12_2$.

Though not shown in FIG. 2, the ECU $12_2$ may include, or may be coupled to, an interface for the display of a barotrauma notification output. For example, the ECU $12_2$ may include a light, display, speaker, or other output mechanism for notifying a user that a tissue pop event has been detected. The ECU $12_2$ may further include an output mechanism to inform a user when ablation energy is no longer being provided to the ablation catheter 26.

Depending on the output capabilities of the ECU $12_2$, the ablation logic 18 and the detection logic 20 may differ from that described with respect to FIGS. 1, 2, and 3. For example, an embodiment of the ablation logic 18 may be configured to direct ablation energy to a "dummy" load when a tissue pop event is detected, rather than disabling the ablation generator 24. In addition, in an embodiment, the detection logic 20 may not include the ability to generate a notification output, or the notification output may simply be to inform the ablation logic that a tissue pop event has been detected.

The system 13 advantageously allows tissue pop to be detected using traditional ablation components (i.e., the ablation generator 24 and the ablation catheter 26) with the addition of the ECU $12_2$, the signal processing hardware 28, and the transducer 30. Accordingly, tissue pop detection can be added to known EP labs without affecting the operation of any of the other systems in the lab.

Figure 5:
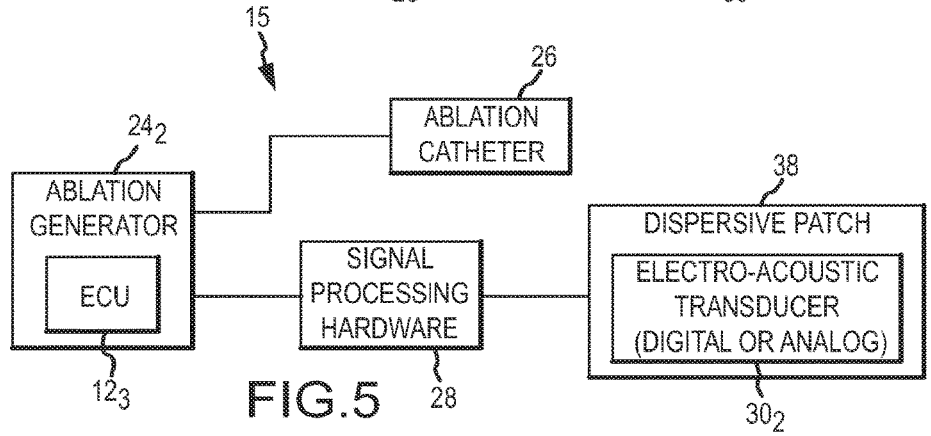
FIG. 5 is a schematic and block diagram view of another system for automatically detecting a myocardial barotrauma event during an ablation procedure.
Figure 6:
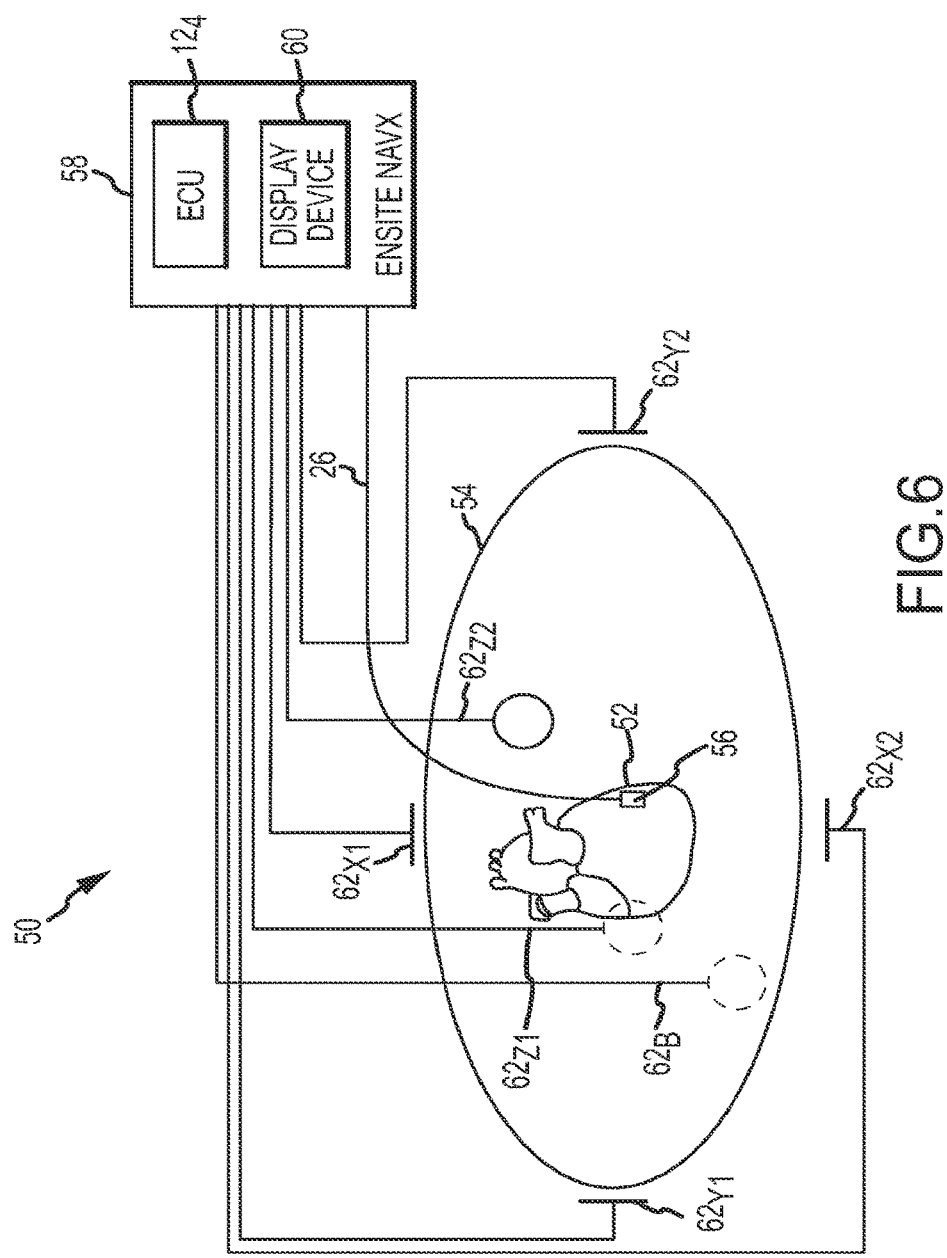
FIG. 6 is a schematic and diagrammatic view of an exemplary embodiment of the system of FIG. 1.

FIG. 5 is a schematic and block diagram view of a system 15 for automatically detecting a tissue pop event during an ablation procedure. The system 15 includes an ablation generator $24_2$, an ECU $12_3$, the ablation catheter 26, the signal processing hardware 28, and an electro-acoustic transducer $30_2$ incorporated into an ablation dispersive patch 38. The components of the system 15 have substantially the same elements and functionality as components with the same or similar numerals described above with respect to FIGS. 1-2, except as distinguished below.

The dispersive patch 38 may be placed on the exterior of a patient's body to act as a dispersive/indifferent return for an ablation signal driven through the ablation catheter 26. The electro-acoustic transducer 30 can be physically incorporated into the dispersive patch 38. However, as noted above, the electro-acoustic transducer 30 may also be provided as a mechanically separate apparatus or in some other form.

The ablation generator $24_1$ includes the ECU $12_3$. Otherwise, the ablation generator $24_1$ may be identical to any of the ablation generators 24, $24_1$ shown in the previous systems 10, 11, 13. As described above, the ECU $12_3$ may receive an electrical signal indicative of acoustic activity within a patient's body and monitor the signal for a pre-determined indication of tissue pop. If a tissue pop event is detected, the ECU $12_3$ can disable or reduce the provision of ablation energy from the ablation generator $24_1$ and/or generate an audible, visual, tactile, or other notification output.

In addition to the above-noted signals indicative of acoustic activity, the ECU $12_3$ may also be configured to monitor one or more signals from the ablation catheter 26, such as a signal indicative of the complex impedance of a tissue, the resistive and reactive components thereof, a computation based on a complex impedance (such as, for example only, an electrical coupling index (ECI)), or another signal or measurement, for a pre-determined indication of tissue pop. For example, a tissue sensing circuit, such as a tissue sensing signal source that is configured to generate an excitation signal used in impedance measurements, may be provided in the ablation generator $24_2$, and means, such as a complex impedance sensor, for resolving detected impedance into its component parts, may be provided in the ablation catheter 26. The ECU $12_3$ may receive a signal indicative of a complex impedance or other measurement from the ablation catheter 26, monitor the signal for a pre-determined indication of tissue pop, and generate a notification output when a tissue pop event is detected. The detection of complex impedance, and the components necessary for such detection, are described in greater detail in, for example, U.S. patent application Ser. No. 12/946,941, and U.S. patent application Ser. No. 12/253,637, both of which are hereby incorporated by reference in their entireties as though fully set forth herein.

The ECU $12_3$ may also be configured to monitor signals generated or received by the ablation generator $24_2$. For example, the ECU $12_3$ may monitor the power output or impedance of the ablation generator $24_2$ for a pre-determined indication of tissue pop, such as an amplitude spike in the monitored signal.

Though not shown in FIG. 5, the ablation generator $24_2$ may include, or may be coupled to, an interface for the display of a barotrauma notification output. For example, the ablation generator $24_2$ may include a light, display, speaker, or other output mechanism for notifying a user that a tissue pop event has been detected.

It should be understood that the different configurations described above in the systems 10, 11, 13, 15 for automatic detection of tissue pop are not mutually exclusive, and thus may be used in combination with each other. For example, a single system may include an external electro-acoustic transducer configured to be placed on the body of a patient, a medical device including another electro-acoustic transducer configured to be placed within the body of the patient, an ablation catheter including components necessary for monitoring a complex impedance, and an ECU capable of monitoring signals from each of the transducers, from the complex impedance detection components of an elongate medical device, and/or signals from or within an ablation generator for pre-determined indicia of tissue pop.

FIG. 6 is a schematic and diagrammatic view of an exemplary embodiment of a portion of the system of FIG. 1, designated system 50, for automatically detecting a tissue pop event in a heart 52 of a patient 54 during an ablation procedure. The system 50 includes an ablation catheter 26 with one or more electrodes 56, a system 58 for visualization, mapping, and navigation of internal body structures, an ECU $12_4$, a display device 60, and a number of patch electrodes $62_B$, $62_{X1}$, $62_{X2}$, $62_{Y1}$, $62_{Y2}$, $62_{Z1}$, and $62_{Z2}$.

The electrodes 56 are provided for a variety of diagnostic and therapeutic purposes including, for example, electrophysiological studies, catheter identification and location, pacing, cardiac mapping, and ablation. In an embodiment, the catheter 26 can include an ablation tip electrode (not shown) at the distal end of the catheter 26, and one or more ring electrodes (illustrated diagrammatically as electrode 56). It should be understood, however, that the number, shape, orientation, and purpose of the electrodes 56 may vary.

The system 58 is provided for visualization, mapping, and/or navigation of internal body structures and may be referred to herein as "the navigation system". The navigation system 58 may comprise an electric field-based system, such as, for example, an EnSite™ Velocity™ cardiac electro-anatomic mapping system running a version of EnSite™ NavX™ navigation and visualization technology software commercially available from St. Jude Medical, Inc., of St. Paul, Minn. and as also seen generally by reference to U.S. Pat. No. 7,263,397, or U.S. Patent Application Publication No. 2007/0060833, both hereby incorporated by reference in their entireties as though fully set forth herein. In other exemplary embodiments, however, the navigation system 58 may comprise systems other than electric field-based systems. For example, the navigation system 58 may comprise a magnetic field-based system such as the Carto™ system commercially available from Biosense Webster, and as generally shown with reference to one or more of U.S. Pat. Nos. 6,498,944; 6,788,967; and 6,690,963, the disclosures of which are hereby incorporated by reference in their entireties as though fully set forth herein. In another exemplary embodiment, the navigation system 58 may comprise a magnetic field-based system based on the Mediguide™ technology available from St. Jude Medical, Inc., and as generally shown with reference to one or more of U.S. Pat. Nos. 6,233,476, 7,197,354 and 7,386,339, the disclosures of which are hereby incorporated by reference in their entireties as though fully set forth herein. In yet another embodiment, the navigation system 58 may comprise a combination electric field-based and magnetic field-based system, such as, for example and without limitation, the system described in pending U.S. patent application Ser. No. 13/231,284, or the Carto™ 3 system commercially available from Biosense Webster, and as generally shown with reference to U.S. Pat. No. 7,536,218, both of which disclosures are hereby incorporated by reference in their entireties as though set fully forth herein. In yet still other exemplary embodiments, the navigation system 58 may comprise or be used in conjunction with other commonly available systems, such as, for example and without limitation, fluoroscopic, computed tomography (CT), and magnetic resonance imaging (MRI)-based systems. For purposes of clarity and illustration only, the navigation system 58 will be described hereinafter as comprising an electric field-based system, such as, for example, the EnSite™ NavX™ system identified above.

With the exception of the patch electrode $62_B$ called a "belly patch," the patch electrodes 62 are provided to generate electrical signals used, for example, in determining the position and orientation of the catheter 26 and in the guidance thereof. In one embodiment, the patch electrodes 62 are placed generally orthogonally on the surface of the body 54 and are used to create axes-specific electric fields within the body 54. For instance, in one exemplary embodiment, patch electrodes $62_{X1}$, $62_{X2}$ may be placed along a first (x) axis. Patch electrodes $62_{Y1}$, $62_{Y2}$ may be placed along a second (y) axis, and patch electrodes $62_{Z1}$, $62_{Z2}$ may be placed along a third (z) axis. Each of the patch electrodes 62 may be coupled to a multiplex switch (not shown). In an exemplary embodiment, the ECU 12 is configured, through appropriate software, to provide control signals to the multiplex switch to thereby sequentially couple pairs of electrodes 62 to a signal generator (also not shown). Excitation of each pair of electrodes 62 (e.g., in either orthogonal or non-orthogonal pairs) generates an electrical field within the patient's body 54 and within an area of interest such as the heart 52. Voltage levels at non-excited electrodes 62, which are referenced to the belly patch $62_B$, are filtered and converted and provided to ECU 12 for use as reference values.

In addition to their functions in positioning and guidance, the patch electrodes 62 can also contain components to perform additional functions. For example, one or more of the patch electrodes 62 can contain an electro-acoustic transducer for, among other things, detection of tissue pop events within the heart 52 during an ablation procedure. An exemplary embodiment of such a patch electrode will be described in greater detail in conjunction with FIG. 7.

As noted above, one or more electrodes 56 are mounted in or on the catheter 26. In an exemplary embodiment, at least one of the electrodes comprises a positioning electrode and is configured to be electrically coupled to the navigation system 58 (i.e., the electrode 56 diagrammatically shown in FIG. 6). With a positioning electrode 56 electrically coupled to the ECU 12, the electrode 56 is placed within electrical fields created in the body 54 (e.g., within the heart 52) by exciting the patch electrodes 62. The positioning electrode 56 experiences voltages that are dependent on the position of the positioning electrode 56 relative to the locations of the patch electrodes 62. Voltage measurement comparisons made between the electrode 56 and the patch electrodes 62 can be used to determine the position of the positioning electrode 56 relative to the heart 52 or other tissue. Movement of the positioning electrode 56 proximate a tissue (e.g., within a chamber of the heart 52) produces information regarding the geometry of the tissue. This information may be used, for example, to generate models and maps of anatomical structures. Information received from the positioning electrode 62 can also be used to display on a display device, such as display device 60, the location and orientation of the positioning electrode 56 and/or the tip of the catheter 26 relative to the heart 52 or other tissue. Accordingly, among other things, the ECU 12 of the navigation system 58 provides a means for generating display signals used to the control display device 60 and the creation of a graphical user interface (GUI) on the display device 60.

The ECU $12_4$ may comprise a programmable microprocessor or microcontroller, or may comprise an application specific integrated circuit (ASIC). The ECU $12_4$ may include a an input/output (I/O) interface through which the ECU $12_4$ may receive a plurality of input signals including, for example, signals generated by patch electrodes 62 and the positioning electrode 56 (among others), and generate a plurality of output signals including, for example, those used to control the display device 60, other user interface components, and an ablation generator (not shown in FIG. 6). The ECU $12_4$ may be configured to perform various functions, such as those described in greater detail above and below, with appropriate programming instructions or code (i.e., software). Accordingly, the ECU $12_4$ is programmed with one or more computer programs encoded on a computer-readable storage medium for performing the functionality described herein. For example, as described above in conjunction with FIGS. 1-5, the ECU $12_4$ can be configured to execute an embodiment of detection logic 20 to automatically detect a pre-determined indication of a tissue pop event on a signal generated by an electro-acoustic transducer, a complex impedance sensor, an ablation generator, or another component.

In operation, the ECU $12_4$ generates signals to selectively energize the patch electrodes 62. The ECU $12_4$ receives position signals (location information) from the catheter 26 (and particularly the positioning electrode 56) reflecting changes in voltage levels on the positioning electrode 56 and from the non-energized patch electrodes 62. The ECU $12_4$ uses the raw positioning data produced by the patch electrodes 62 and positioning electrode 56 and corrects the data to account for respiration, cardiac activity, and other artifacts using known techniques. The corrected data may then be used by the ECU $12_4$ in a number of ways, such as, for example and without limitation, to guide an ablation catheter to a treatment site, to create a model of an anatomical structure, to map electrophysiological data on an image or model of the heart 52 or other tissue generated or acquired by the ECU $12_4$, or to create a representation of the catheter 26 that may be superimposed on a map, model, or image of the heart 52 generated or acquired by the ECU $12_4$.

Figure 7:
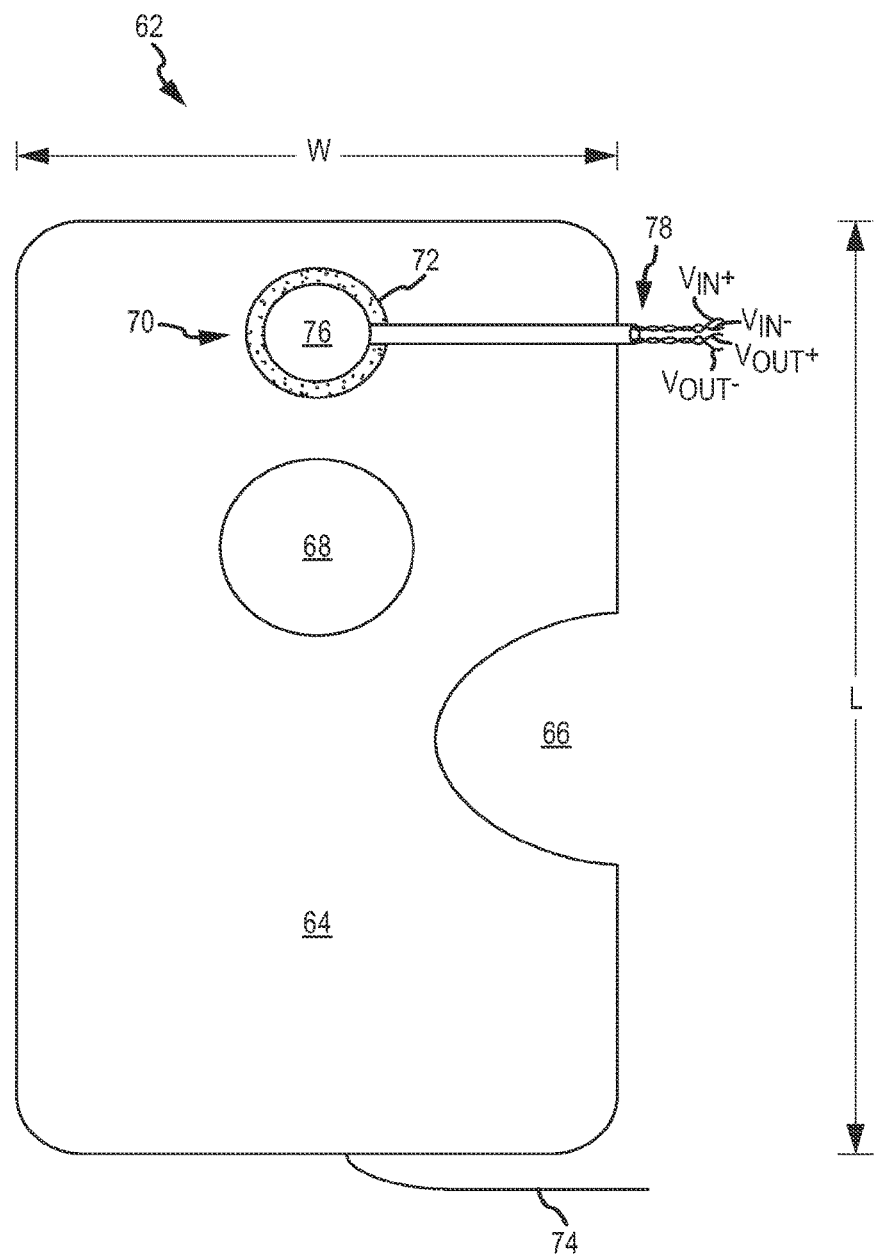
FIG. 7 is a schematic and diagrammatic view of an embodiment of an electro-acoustic transducer incorporated into a patch for an electrical impedance-based medical device navigation system.

FIG. 7 is a diagrammatic view of an exemplary embodiment of a patch electrode 62 for use in a system for automatically detecting tissue pop during an ablation procedure. The patch 62 includes a main portion 64, two cutouts 66, 68, an embodiment of the electro-acoustic transducer 30 (labeled transducer 70), and an isolation barrier 72.

The main portion 64 of the patch 62 has a width W, a length L, and can include one or more electrodes, an array of electrode contact points, related circuitry, and/or required layers and materials as known in the art. For example and without limitation, main patch portion 62 can be constructed as described in U.S. Pat. No. 7,996,055, or as in pending U.S. patent application Ser. No. 12/981,150, both of which are hereby incorporated by reference in their entireties as though fully set forth herein. The electrodes (not shown) included in main portion 64 can be electrically coupled to a navigation system through electrode wiring 74. In an embodiment, the main portion 64 has a width W of about 75 millimeters (mm) and a length L of about 175 mm.

The two cutouts 66, 68 provide a location through which additional electrodes or sensors may be applied to the body of a patient. In an embodiment, ECG electrodes can be placed in the cutouts 66, 68.

The electro-acoustic transducer 70 includes an auscultation membrane 76, which can be encased or enclosed in a housing or other structure. The transducer 70 can be electrically coupled with a navigation system or other system through electro-acoustic wiring 78. In the illustrated embodiment, the electro-acoustic wiring 78 includes four lines, $V_{IN+}$, $V_{IN-}$, $V_{OUT+}$, and $V_{OUT-}$. The electro-acoustic wiring 78 can be connected to, for example, a navigation system or another system. In another embodiment (not shown), the electro-acoustic wiring 78 may be sheathed together with the electrode wiring 74, terminating in a single connector. The transducer 70 can be, for example, a ds32a Digital Electronic Stethoscope commercially available from Thinklabs Medical, LLC of Centennial, Colo. Alternatively, the transducer 70 can comprise electronic components from the ds32a Digital Electronic Stethoscope, placed into a customized form factor.

An isolation barrier 72 is provided to electrically isolate the transducer 70 from the main portion 64 of the patch 62. The barrier 72 can be made of an electrically-insulative material suitable for operating room use and can have dimensions tailored to the dimensions of the patch main portion 64 and the transducer 70.

The electro-acoustic transducer 70 is configured to translate acoustic activity from within the body of a patient into an electrical signal. In an embodiment, the transducer 70 can also include signal processing capability (either hardware or software) for, e.g., filtering, attenuating, and/or amplifying the output electrical signal. The transducer 70 can be integrated with the patch main portion 64 during construction of the patch 62, or can be an independent device that is separable from the patch 62 (substantially as shown).

During an ablation procedure, one or more transducers integrated with one or more patches coupled with the exterior of the patient's body can be used to electronically "listen" for tissue pop events. In an embodiment, patches 62 are placed along multiple axes on a patient's body: X-axis patch electrodes $62_{X1}$, $62_{X2}$ are placed on the left and right sides of the patient's ribcage, respectively, Y-axis patch electrodes $62_{Y1}$, $62_{Y2}$, are placed on the patient's neck and leg, respectively, and Z-axis patch electrodes $62_{Z1}$, $62_{Z2}$ are placed on the patient's chest and back, respectively. Transducers can be integrated or coupled with any or all of the patches 62 in such an embodiment, though particular locations may result in more reliable tissue pop detection. For example, a transducer in the chest patch $62_{Z1}$ might have sufficient acoustic resolution over the entire heart, and could be used to detect tissue pop in any chamber. But the side patches $62_{X1}$, $62_{X2}$ might have higher resolution in chambers on their respective sides on the body, and could be used to focus on one side of the heart or the other. In a multi-transducer embodiment, a user or an ECU can select which transducer (or transducers) is actively used to "listen" for tissue pop.

In an embodiment of any of the systems 10, 11, 13, 15, and 50 that includes a magnetic field based position and navigation system, such as in above-incorporated U.S. Pat. Nos. 6,233,476, 7,197,354, and 7,386,339, an electro-acoustic transducer can be incorporated into a reference sensor placed on the body of the patient. Such a reference sensor can include many or all of the transducer-related features included in the patch 62, such as an auscultation membrane, housing, isolation barrier, and signal wiring.

Figure 8:
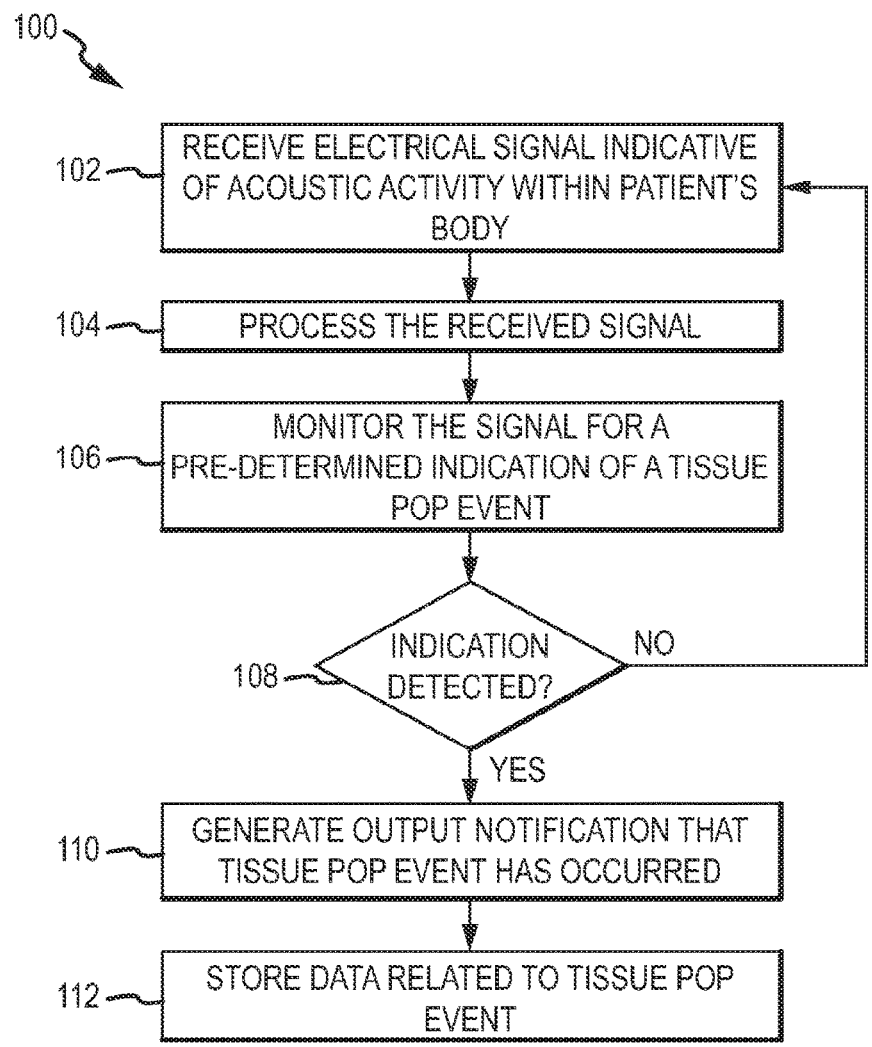
FIG. 8 is a flow chart illustrating a method of automatically detecting a myocardial barotrauma event during an ablation procedure.

FIG. 8 is a flow chart illustrating a computer-implementable method 100 of automatically detecting a tissue pop event. The method 100 may be stored as instructions or logic in computer-readable memory (such as memory 16) for execution by an electronic control unit (such as any of ECU 12, $12_1$, $12_2$, $12_3$, and $12_4$). For example, the ECU 12 can execute an embodiment of detection logic 20 and an embodiment of ablation logic 18 to perform the steps of the method 100.

The first step 102 of the method 100 includes receiving an electrical signal indicative of acoustic activity within a patient's body. The signal can be received from an electro-acoustic transducer, such as, for example only, a transducer 70 integrated into a patch or body surface electrode 62. Depending on the location of the tissue on which the ablation procedure is being performed, the transducer 70 may be placed in a variety of different locations on the body of the patient. For example, during an ablation procedure on the right atrium of the patient's heart, a transducer in a patch $62_{X1}$ on the patient's right side can be selected and used to monitor the acoustic activity in the heart. A transducer in a patch on the patient's left side, $62_{X2}$, chest, $62_{Z1}$, or back, $62_{Z2}$, could also be selected and used.

The next step 104 includes processing the received signal. The signal processing step 104 can include filtering, attenuating, and/or amplifying the signal and can be performed by hardware, software, or a combination of both. In an embodiment, the processing step 104 includes a first substep of applying a frequency filter to the signal and a second substep of applying an amplification algorithm to the filtered signal. The filtering substep can include eliminating one or more particular frequencies or frequency ranges in the received signal. For example, the received signal might have components caused by excitation signals from a navigation system (e.g., driven between electrodes in patches 62) and by the signal transmitted through an ablation catheter as ablation energy. In an embodiment, the excitation signals may have a frequency of about 5.68 kilohertz (kHz) or 8 kHz and the ablation signal may have a frequency of about 485 kHz. In contrast, the signal spike caused by a tissue pop event is generally detectable in frequencies of about 500 Hz. Thus, in an embodiment, the filtering sub-step can include applying a low-pass filter to eliminate components in the received electrical signal having a frequency above about 5 kHz and a high-pass filter to eliminate components in the received electrical signal having a frequency below about 300 Hz.

The second filtering sub-step can include applying an amplification algorithm designed to amplify an occurrence of a predetermined indication of a tissue pop event so that a tissue pop event is easier to distinguish from other biological activity. In an embodiment, the amplification algorithm applied to the filtered signal can have the form shown in Equation (1) below:

$$V_{OUT}(t)=(V_{IN}(t)-V_{IN}(t-t_1))^3 \qquad \text{(Eq. 1)}$$

Where $V_{OUT}(t)$ is the continuous output from the amplification algorithm, $V_{IN}(t)$ is the continuous input to the algorithm (i.e., the received, and possibly filtered, signal), and $V_{IN}(t-t_1)$ is a time-shifted version of the continuous input. The purpose of the algorithm shown in Equation (1) is to cancel out "normal"—i.e., periodic and recurring—acoustic activity and to amplify abnormal activity, such as tissue pop. Accordingly, $t_1$ can be configured to be approximately equal to the period of the patient's heartbeat to cancel out signal portions caused by normal heart activity. In an embodiment, the "normal" acoustic activity can be determined during a preliminary portion of a procedure, stored, and then be continuously compared with the received signal (i. (i.e., $V_{IN}(t)$).

After the signal is processed, the method 100 continues to the next step 106, which includes monitoring the signal for a pre-determined indication of a tissue pop event. The pre-determined indication can be a particular pattern in the received electrical signal. In an embodiment, the pre-determined indication can be a spike in the signal with a relatively short duration. For example only, the pre-determined indication can be a spike with a duration of about 2-3 milliseconds or less and approximately the same amplitude as a wave in the electro-acoustic signal caused by a contraction of a heart chamber. In an embodiment, the threshold amplitude for a tissue pop event—i.e., the minimum amplitude required for a signal spike to be reported as tissue pop—is configurable by a user of the system.

Steps 102, 104, and 106 can involve multiple electro-acoustic signals from multiple electro-acoustic transducers. For example, each of a patch on the patient's right side, $62_{X1}$, left side, $62_{X2}$, chest, $62_{Z1}$, or back, $62_{Z2}$, can be equipped with a stethoscope or other electro-acoustic transducer, each of which can be electrically coupled with the ECU 12. The ECU 12 can perform steps 102 (receive), 104 (process), and 106 (monitor) on a signal from each transducer, thus using multiple transducers simultaneously to automatically detect a tissue pop event. Alternatively, the ECU 12 can enable only a particular transducer or set of transducers at a time, depending on the location of the tissue being ablated relative to the respective locations of the transducers. The ECU 12 (via detection logic 20) can be programmed to automatically select the transducer or transducers most likely to "hear" a tissue pop event based on the number of available transducers, the locations of those transducers, and the position and orientation of the ablation catheter. For example, if the tip of the ablation catheter is in the right atrium (as indicated by the position and orientation of one or more sensors on the catheter), a transducer 70 on right patch $62_{X1}$ can be activated by the ECU 12 to "listen" for tissue pop.

Steps 102, 104, and 106 can be performed continuously during an ablation procedure—i.e., the ECU 12 can continuously receive one or more electro-acoustic signals, process the signals, and monitor the signals for a pre-determined indication of a tissue pop event. If the ECU detects a pre-determined indication of a tissue pop event in one or more electro-acoustic signals, (shown as query step 108), the method advances to steps 110 and 112. In an embodiment, the ECU 12 may require detection of a tissue pop event according to signals from two or more transducers before advancing to steps 110 and 112. In operation, even as the method advances to steps 110 and 112 after a tissue pop event is detected, the ECU 12 can continue to receive, process, and monitor one or more signals according to steps 102, 104, and 106.

Step 110 includes generating a notification output to alert the physician or electrophysiologist that a tissue pop event has occurred. The notification mechanism driven by the output can be any output mechanism capable of alerting the electrophysiologist or physician that tissue pop has occurred and can be visual, audible, tactile, or a combination. For example only, the notification can be implemented with an LED or other light, a binary indicator (i.e., ON or OFF) on a computer display or other display (i.e., a "virtual LED"), a continuous display on a computer display or other display, and/or an audible alarm. The content of a visual embodiment of notification 34 can be discrete or continuous in nature and can include, but is not limited to, an alert light, an alert message, an alert sound, and a continuous waveform. In an embodiment, when a tissue pop event is detected, the notification can comprise a pop-up window in a computer display that shows a waveform of the electrical signal from around the time that the tissue pop event was detected. Such an alert may allow the physician or electrophysiologist to, for example only, cease RF delivery, use lower power, increase irrigation, and/or increase catheter tip movement.

In an embodiment, step 110 can further include disabling an ablation generator—i.e., the ECU 12 can disable the ablation generator 24 by executing ablation logic 18. Alternatively, the power to the ablation generator can be reduced or altered.

Step 112 includes storing data related to the tissue pop event. For example, the ECU 12 can store data in data storage memory 22. Stored data can include a portion of one or more of the received electrical signals. For example, a portion of the electrical signal starting at a pre-determined amount of time before the tissue pop event and ending at a pre-determined amount of time after the tissue pop event can be saved. In an embodiment, the signal portion stored in for an event can have a duration of about 20 seconds—10 seconds before the event through 10 seconds after the event. Stored data can also include other information about the procedure, patient, or conditions surrounding a tissue pop event. For example, other stored data can include, without limitation, position and orientation (P&O) data showing the location of an ablation catheter when a tissue pop event occurred, other patient data (e.g., ECG), and ablation generator settings. The stored data can be reviewed by a physician after the procedure to design a more effective treatment plan for the patient. The stored data can also be used by the physician or electrophysiologist performing the ablation procedure to better understand the conditions resulting in tissue pop to avoid future tissue pop events.

It should be understood that the specific sequence set forth in steps 102 through 112 is exemplary only and is for description purposes only. In some embodiments, the storing step 112 may occur continuously in time as various EP, P&O, transducer and other data is produced and collected, and is not necessarily stored only after a notification step is performed. For further example, the evaluation/decision step 108, in one embodiment, employs an algorithm that looks back to data acquired in a previous sample. It should be understood that other detection algorithms may likewise use previously acquired data.

It should also be understood that the steps of method 100 may be adapted to the type and source of signal(s) being monitored for tissue pop, such as signals from internal and external electro-acoustic transducers (i.e., inside or outside the body of a patient), complex impedance signals, power and impedance signals from an ablation generator, and the like. Accordingly, the steps described above are for the purposes of illustration only.

Figure 9A:
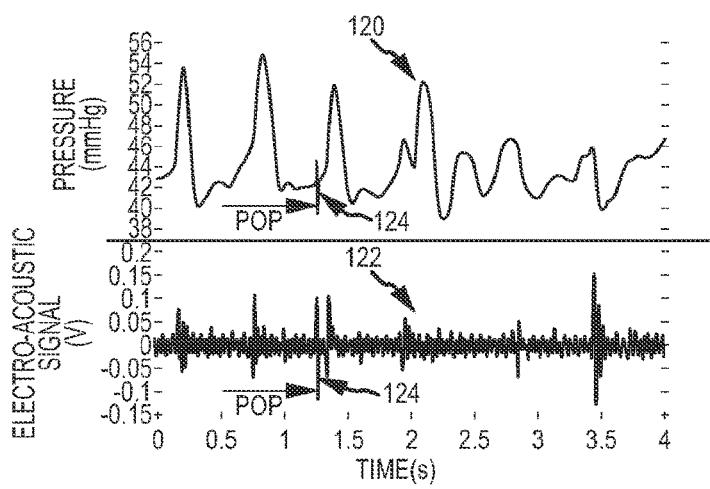
FIGS. 9A-9C are plots illustrating electrical signals indicative of a tissue pop event.
Figure 9B:
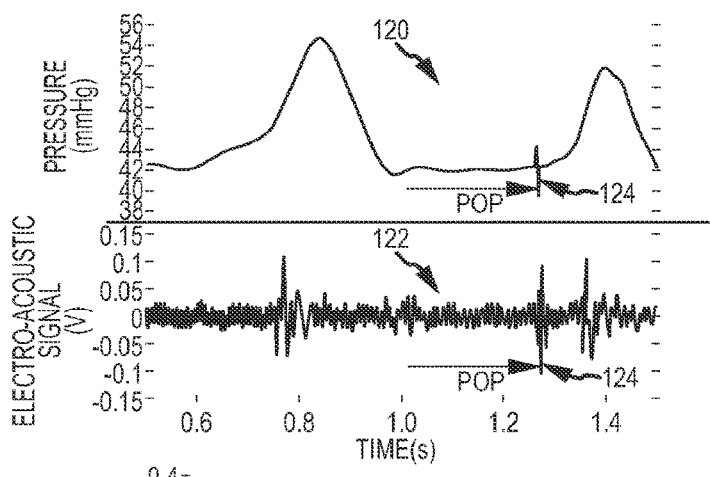
Figure 9C:
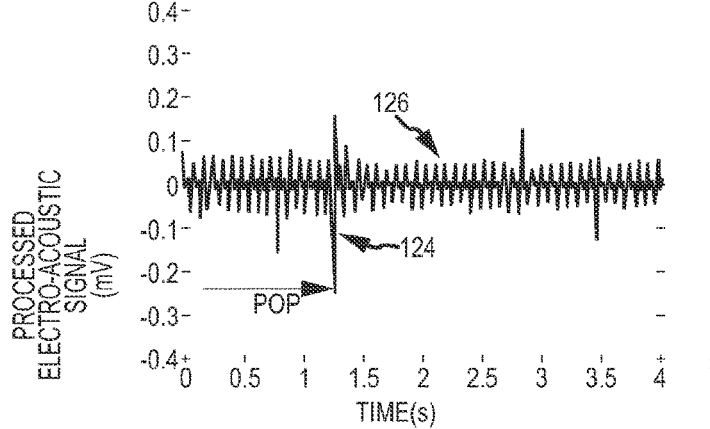

FIGS. 9A-9C are plots illustrating indicia of a tissue pop event that can be automatically detected by a system (such as system 10, 11, 13, 15, or 50) executing method 100. FIG. 9A includes a first waveform 120 of a signal indicative of pressure within a heart chamber (as captured by a sensor on an intracardiac catheter) and a second waveform 122 of an electrical signal indicative of acoustic activity in and around the same heart chamber (as captured by an extra-body electro-acoustic transducer). Both waveforms 120, 122 include a sharp spike 124 that indicates that a tissue pop event has occurred.

FIG. 9B includes the same waveforms 120, 122 as FIG. 8A, but illustrates a shorter duration of the waveforms to highlight the temporal difference between the tissue pop spike and other signal portions. In both the pressure waveform 120 and the electro-acoustic waveform 122, the tissue pop spike 124 has a shorter duration, and thus more rapid rise, than other rises and spikes in the signals. This unique spike—short in duration, relatively high amplitude—can be distinguished from spikes related to other biological phenomena, and thus can be programmed into computer-readable memory or an ECU as a pre-determined indication of a tissue pop event.

It should be noted that although both the acoustic-based signal and the pressure-based signal show the tissue pop event, the acoustic signal may be preferred because it can be captured with noninvasive methods. For example, an acoustic signal can be captured with an extra-body transducer placed on the patient, whereas the pressure reading may require insertion of an additional catheter into the patient's vasculature. However, it should be understood that noninvasive pressure-based signals may also be obtained and monitored for tissue pop according to the present disclosure.

FIG. 9C includes a waveform 126 of a processed version of the electro-acoustic signal illustrated in FIGS. 8A and 8B. Waveform 126 is the result of an amplification algorithm being applied to the electro-acoustic signal of the general form shown in Equation (1) above of the specific form of Equation (2) below:

$$V_{OUT}(t)=(V_{IN}(t)-V_{IN}(t-1))^3 \qquad \text{(Eq. 2)}$$

The amplification algorithm amplifies the tissue pop spike 124 in both positive and negative directions. As a result, the tissue pop indication can be even more easily distinguished from other rises and spikes in the electro-acoustic signal.

Automatic acoustic detection of tissue pop events through the systems and method described herein provides numerous advantages over known manual methods. First, a physician is more likely to be aware of a tissue pop event than if the physician had merely relied on hearing the pop him or herself or feeling the pop through the ablation catheter. As a result, the physician is more likely to design a proper post-operation treatment plan for the patient that takes a tissue pop occurrence into account. Second, the system can store data related to one or more tissue pop events, allowing a physician to study those data and learn about particular conditions leading to tissue pop. And third, acoustic detection of tissue pop is noninvasive.

The systems and methods described herein may find use in diagnosis of conditions and events other than tissue pop, and accordingly are not limited to use to diagnose tissue pop. For example, systems 10, 11, 13, 15, and 50 and method 100 can all be used for automatic detection of heart murmur, arrhythmia, or telltale acoustic signs of heart disease. Such other conditions can be tested and diagnosed during an ablation procedure, or as part of a separate procedure. In some embodiments, certain aspects of the systems and methods can be customized in manufacture or by the user for detection of a selected condition. For example, filter frequencies, transducer sampling rate, and detection notification threshold can all be modified, as well as other system settings and characteristics. Furthermore, the system can be configured to multitask—i.e., to monitor for acoustic activity indicative of several conditions and events simultaneously or in sequence.

In accordance with an embodiment, a system includes a computer storage medium having a computer program encoded thereon, where the computer program includes code configured to receive an electrical signal indicative of acoustic activity within the patient, monitor the signal for a pre-determined indication of a barotrauma event, and generate a notification output when the pre-determined indication is detected. Such embodiments may be configured to execute one or more processors, multiple processors that are integrated into a single system or are distributed over and connected together through a communications network, and where the network may be wired or wireless.

It should be understood that an electronic control unit as described above may include conventional processing apparatus known in the art, capable of executing pre-programmed instructions stored in an associated memory, all performing in accordance with the functionality described herein. It is contemplated that the methods described herein may be programmed, with the resulting software being stored in an associated memory and where so described, may also constitute the means for performing such methods. Implementation of an embodiment of the invention, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A system for detecting a myocardial barotrauma event in a tissue of a body during an ablation procedure, comprising:
   an electronic control unit (ECU);
   a computer-readable memory coupled with said ECU; and
   detection logic stored in said memory configured to be executed by said ECU, said detection logic configured to:
     receive an electrical signal indicative of acoustic activity that represents the myocardial barotrauma event within the body, wherein the electrical signal indicative of acoustic activity that represents the myocardial barotrauma event is received from one of a plurality of electro-acoustic transducers configured to be placed in communication with an external surface of the body, wherein the one of the plurality of electro-acoustic transducers is selected by the ECU as being most likely to register a tissue pop event based on a number of available electro-acoustic transducers, the location of the electro-acoustic transducers, and a position and orientation of an ablation catheter disposed in the body during the ablation procedure;
     monitor said signal for a pre-determined indication of a myocardial barotrauma event; and
     generate a notification output when said pre-determined indication is detected.

2. The system of claim 1, wherein said detection logic is further configured to apply an amplification algorithm to said signal, said amplification algorithm being configured to amplify an occurrence of said pre-determined indication.

3. The system of claim 1, further comprising storage memory coupled with said ECU, wherein said detection logic is further configured to store data in said storage memory related to a barotrauma event when said pre-determined indication is detected.

4. The system of claim 3, wherein said data comprises a portion of said signal beginning at a first time before said barotrauma event and ending at a second time after said barotrauma event.

5. The system of claim 1, wherein said pre-determined indication has a temporal duration of about three milliseconds or less.

6. The system of claim 1, wherein said notification output comprises a visual notification.

7. The system of claim 6, wherein said visual notification comprises a display of said signal.

8. The system of claim 1, wherein said notification output comprises an auditory notification.

9. The system of claim 1, further comprising ablation logic stored in said memory configured to be executed by said ECU, said ablation logic configured to disable an ablation generator when said pre-determined indication is detected.

10. The system of claim 1, wherein the electro-acoustic transducer is incorporated into an ablation dispersive patch configured to be coupled with the external surface of the body.

11. The system of claim 1, wherein the electro-acoustic transducer is incorporated into an electrode patch configured to be coupled with the external surface of the body and configured to be used with a medical device positioning and navigation system.

12. The system of claim 11, wherein the received electrical signal indicative of acoustic activity within the body is one of a plurality of electrical signals indicative of acoustic activity within the body that are received from a plurality of electro-acoustic transducers incorporated into a plurality of electrode patches configured to be coupled with the external surface of the body.

13. The system of claim 1, wherein:
   the electro-acoustic transducer is incorporated into an ablation dispersive patch;
   the ablation dispersive patch is configured to receive an ablation signal; and
   the electro-acoustic transducer is configured to receive the electrical signal indicative of acoustic activity that represents the myocardial barotrauma event.

14. The system of claim 13, further comprising filter, wherein the low-pass filter filters the electrical signal indicative of acoustic activity that represents the myocardial barotrauma event to eliminate frequencies generated by the ablation dispersive patch.

* * * * *